(12) United States Patent
Eversheim et al.

(10) Patent No.: US 7,374,771 B2
(45) Date of Patent: May 20, 2008

(54) USE OF SILOXANES AS VAPORIZABLE CARRIERS

(75) Inventors: Hubertus Eversheim, Wermelskirchen (DE); Martin Kropfgans, Odenthal (DE); Sabine Nienstedt, Bonn (DE); Horst Lange, Bochum (DE)

(73) Assignee: GE Bayer Silicones GmbH & Co., KG, Leverkusen (DE)

( * ) Notice: Subject to any disclaimer, the term of this patent is extended or adjusted under 35 U.S.C. 154(b) by 21 days.

(21) Appl. No.: 10/495,343

(22) PCT Filed: Nov. 12, 2002

(86) PCT No.: PCT/EP02/12596

§ 371 (c)(1),
(2), (4) Date: Oct. 26, 2004

(87) PCT Pub. No.: WO03/042221

PCT Pub. Date: May 22, 2003

(65) Prior Publication Data

US 2005/0069564 A1    Mar. 31, 2005

(30) Foreign Application Priority Data

Nov. 13, 2001   (DE) ................ 101 55 512

(51) Int. Cl.
*A61K 8/25* (2006.01)
(52) U.S. Cl. .............. 424/401; 424/64; 424/70.12; 556/450; 556/462; 556/465; 556/466
(58) Field of Classification Search .............. None
See application file for complete search history.

(56) References Cited

U.S. PATENT DOCUMENTS

| 4,376,087 | A |   | 3/1983 | Poliniak |
| 5,002,762 | A |   | 3/1991 | Bolich, Jr. |
| 5,084,577 | A |   | 1/1992 | Bolich, Jr. |
| 5,922,309 | A |   | 7/1999 | Brewster ............ 424/65 |
| 6,197,911 | B1 | * | 3/2001 | Richard et al. ............ 528/15 |
| 6,437,163 | B1 | * | 8/2002 | Branlard et al. ............ 556/450 |
| 2004/0197284 | A1 | * | 10/2004 | Auguste ............ 424/70.12 |

FOREIGN PATENT DOCUMENTS

| CN | 1247868 |   | 3/2000 |
| EP | 0 980 855 A2 |   | 8/1999 |
| FR | 2771003 |   | 5/1999 |
| JP | 55-020737 |   | 2/1980 |
| JP | 2000-204398 |   | 7/2000 |
| JP | 2005232235 A | * | 9/2005 |
| WO | WO 98/32418 |   | 7/1998 |

OTHER PUBLICATIONS

Computer translation of JP 2000-204398.*
Abstract for "Effect of Hydrochloric Acid on the Hydrolytic Polycondensation of Bifunctional Organochlorosilanes with Chlorotrimethylsilane" authored by Kopylov et al. and published in Zhurnal Obshchei Khimii (1991), 61(6), 1378-83.*
T Koini, M.D. Berthiaume, A. Huber, *SOFW-Journal*, 125$^{th}$ vol. 4/99, 22.
W. Noll, *Chemie und Technologie der Silicone*, 2$^{nd}$ Edition, Verlag Chemie Weinheim 1968, p. 216f.
H.-H. Moretto, M. Schulze, G. Wagner, *Ullmann's Encyclopedia of Industrial Chemistry*, 6$^{th}$ Edition 1998, Wiley-VCH, Weinheim.
G. Koerner, *Silicone-Chemie und Technologie*, Symposium, Vulkan-Verlag Essen 1998, p. 3.
Bogdan Marciniec (Ed.), *Comprehensive Handbook on Hydrosilylation*, Pergamon Press, Oxford, 1992, p. 99 ff.

* cited by examiner

*Primary Examiner*—Marc S. Zimmer
(74) *Attorney, Agent, or Firm*—Norris McLaughlin & Marcus PA

(57) ABSTRACT

Cosmetic formulations comprising alkyl-substituted siloxanes as vaporizable carriers.

11 Claims, 1 Drawing Sheet

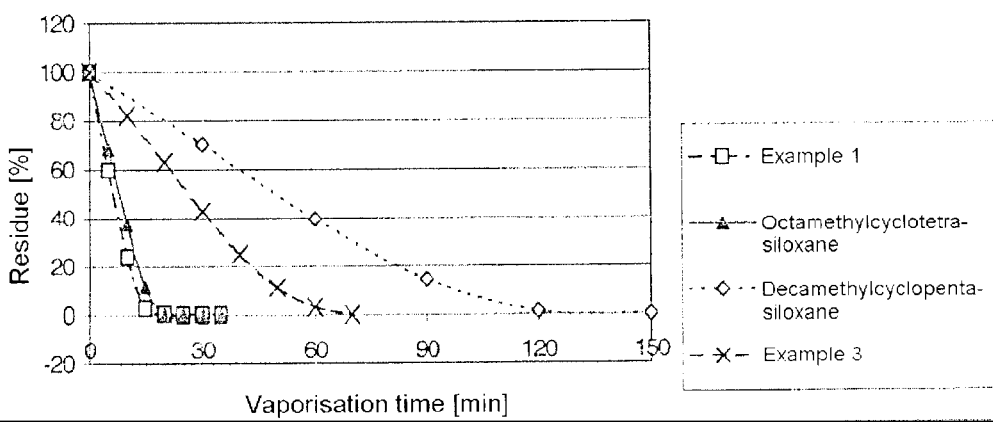

USE OF SILOXANES AS VAPORIZABLE CARRIERS

This is a 371 of PCT/EP02/12596 filed 12 Nov. 2002 (international filing date).

BACKGROUND OF THE INVENTION

Low molecular weight siloxanes have been known for a long time as vaporizable carriers in cosmetic preparations (T. Koini, M. D. Berthiaume, A. Huber in: SÖFW-Journal, 125th volume 4/99, 22). In particular, octamethylcyclotetrasiloxane could be found widely in cosmetic applications due to its relatively high rate of vaporization and its pleasant feel on the skin (Product Description SF 1173, SF 1202, SF 1204, SF 1246 General Electric (GE) Silicones CDS 4958-E/ENG/0797).

In recent times, doubts have been raised concerning the use of octamethylcyclotetrasiloxane in cosmetic formulations from the points of view of physiological compatibility. In animal experiments, reduced fertility has been observed in cases of extreme dosages. For this reason, efforts have recently increasingly been undertaken to replace octamethylcyclotetrasiloxane in cosmetic formulations with suitable components; these substitutes have hitherto not achieved the performance and properties profile of octamethylcyclotetrasiloxane. Thus, firstly, the rate of vaporization of the decamethylcyclopentasiloxane used as substitute for octamethylcyclotetrasiloxane is significantly lower. Secondly, both the linear octamethyltrisiloxane and also decamethyltetrasiloxane do not convey the silky, non-greasy feel on the skin typical of the cyclic siloxanes.

It has hitherto not been possible to develop vaporizable carrier substances which are sufficiently volatile and at the same time exhibit the good feel on the skin of the cyclic siloxanes and thus make it possible to dispense with the use of octamethylcyclotetrasiloxane (=D4) as vaporizable carrier in the manufacture of cosmetic preparations. Vaporizable carriers are to be understood here as meaning siloxanes which have a boiling point at atmospheric pressure of less than 250° C. and a vaporization behaviour measured in accordance with DIN 53249 similar to that of D4.

EP 0 980 885 describes mixtures of volatile siloxanes which can be used in cosmetic formulations. The objective of EP 980 855 is to seek volatile linear siloxanes which have been only 80-85% by weight vaporized after 30 minutes in accordance with DIN 53249.

These siloxanes should thus vaporize more slowly than octamethylcyclotetrasiloxane (=D4).

WO 98-32418 describes transparent antiperspirant gels which may, inter alia, comprise the vaporizable mixtures of the linear siloxanes of EP 980 855 and additionally cyclosiloxane.

However, it gives no indication that alkylsiloxanes with a volatility comparable to that of D4 are preferred or that such compounds have been recognized therein as a replacement for D4.

In contrast to EP 980 855 and WO 98-32418, it was the object of this invention to develop pure substances which can be used as volatile carrier substance in place of D4 particularly in cosmetic formulations, but also in other cleaning formulations, where the vaporization behaviour should resemble as closely as possible that of octamethylcyclotetrasiloxane, remain liquid over large temperature ranges and whose setting point should in particular be at relatively low temperatures. In this connection, it is advantageous that as a result of using pure individual substances, it is possible to reduce the number of substances present in cosmetic formulations. This minimizes interactions of the various substances with one another, meaning that product safety and quality assurance are decisively improved. That is to say, the preferred formulations are the formulations in which the octamethylcyclotetrasiloxane or linear permethylated siloxanes with comparable vaporization behaviour are replaced exclusively by the linear alkylmethylsiloxanes according to the invention in pure form with a content above 85%.

Moreover, the vaporizable siloxanes according to the invention have no or low "whitening". This is understood as meaning the phenomenon, described in U.S. Pat. No. 5,922,309, of white residues on the skin or the textile.

Moreover, it was an object of the invention to develop siloxanes with a silky, non-greasy feel on the skin and with vaporization properties which are similar to those of octamethylcyclotetrasiloxane or exceed them. Octamethylcyclotetrasiloxane has a setting point at a relatively high temperature of 4° C., which may lead to problems during transportation, storage and processing of formulations and raw material, depending on climatic conditions. It was therefore also an aim of this invention to develop siloxanes with a more favourable, lower setting point. In addition, it was an object of the invention to develop siloxanes with good compatibility with cosmetic raw materials.

SUMMARY OF THE INVENTION

Surprisingly, it has been found that selected low molecular weight linear siloxanes modified with short-chain alkyl groups have good vaporization properties which can be controlled through the choice of the alkyl groups, and at the same time have a silky, non-greasy feel on the skin corresponding to that of the cyclic siloxanes.

The siloxanes used according to the invention are the following compounds: 1,1,3,3,3-pentamethyl-1-ethyldisiloxane, 1,1,3,3-tetramethyl-1,3-diethyldisiloxane, 1,1,3,3,3-pentamethyl-1-propyldisiloxane, 1,1,3,3-tetramethyl-1,3-dipropyldisiloxane, 1,1,3,3,3-pentamethyl-1-butyldisiloxane, 1,1,3,3-tetramethyl-1,3-dibutyldisiloxane, 1,1,1,3,5,5,5-heptamethyl-3-ethyltrisiloxane, 1,1,1,5,5,5-hexamethyl-3,3-diethyltrisiloxane, 1,1,3,3,5,5-hexamethyl-1,5-diethyltrisiloxane, 1,1,1,3,5,5,5-heptamethyl-3-propyltrisiloxane, 1,1,1,5,5,5-hexamethyl-3,3-dipropyldisiloxane or 1,1,1,3,5,5,5-heptamethyl-3-butyltrisiloxane, with the proviso that the propyl and butyl groups may be linear or branched substituents as vaporizable carriers in cosmetic formulations.

DETAILED DESCRIPTION

For the purposes of the invention, a vaporizable carrier means a substance with a suitable vaporization behaviour which is introduced into a cosmetic or cleaning formulation. This carrier allows various components to be incorporated into this formulation without separation. The carrier must on the one hand have a certain volatility, but on the other hand must also ensure good application of the total product.

Preference is given to 1,1,1,3,5,5,5-heptamethyl-3-propyltrisiloxane (CAS No. 29054-80-6), 1,1,1,5,5,5-hexamethyl-3,3-diethyltrisiloxane, 1,1,3,3,3-pentamethyl-1-butyldisiloxane, and 1,1,1,3,5,5,5-heptamethyl-3-butyltrisiloxane (CAS No. 18138-63-1). The most preferred siloxane is 1,1,1,3,5,5,5-heptamethyl-3-ethyltrisiloxane (CAS No. 17861-60-8).

The compounds used according to the invention are known per se (W. Noll, Chemie und Technologie der Silicone, 2nd edition, Verlag Chemie Weinheim 1968, p. 216 f.). They can preferably be prepared by addition of alkenes selected in a targeted manner over suitable SiH functional siloxanes and optional subsequent equilibration reactions. An alternative preparation is also through the introduction of the alkyl substituent into chlorosilanes via organometallic reagents (e.g. GRIGNARD and/or WURTZ reagents) with subsequent hydrolysis of the alkylchlorosilane produced by this reaction, preferably methylalkyldichlorosilanes, and the equilibration with the hydrolysis products of other methylchlorosilanes.

The siloxanes used according to the invention are characterized by setting points which are much lower than the freezing point of water, which facilitates transportation and also incorporation and use in cosmetic formulations.

The siloxanes used according to the invention were incorporated into cosmetic formulations and these were then assessed with regard to their feel on the skin by independent subjects. In this connection, the feel on the skin was assessed as being better than in the case of the use of decamethylcyclopentasiloxane. By contrast, with regard to the use of octamethylcyclotetrasiloxane, no significant differences could be observed.

In a preferred method, the compounds used according to the invention can be obtained by distilling a mixture of hexamethyldisiloxane, 1,1,1,3,5,5,5-heptamethyl-3-ethyltrisiloxane and oligomeric compounds, of which the following homologue (1,1,1,3,5,7,7,7-octamethyl-3,5-diethyltetrasiloxane) has a boiling point of >220° C. The silanes used for this reaction are produced as secondary products during the direct synthesis of dimethyldichlorosilane (H.-H. Moretto, M. Schulze, G. Wagner in: Ullmann's Encyclopedia of Industrial Chemistry, Sixth Edition 1998, Wiley-VCH, Weinheim). Cohydrolysis of methylethyldichlorosilane with trimethylchlorosilane produces, for example, suitable mixtures which can be worked-up by distillation to give 1,1,1, 3,5,5,5-heptamethyl-3-ethyltrisiloxane. Surprisingly, it has been found that in this process variant starting from a complex mixture of secondary products following cohydrolysis, the products used according to the invention are accessible in high-purity defined form by equilibration and simple distillation.

Alternatively, mixtures of 1,1,1,3,5,5,5-heptamethyl-3-ethyltrisiloxane and oligomeric compounds can be obtained from a hydrolysate of methylethyldichlorosilane and its subsequent acid-catalysed equilibration with hexamethyldisiloxane (G. Koerner in: Silicone-Chemie und Technologie, Symposium, Vulkan-Verlag Essen 1998, page 3).

It is likewise preferred to obtain the siloxanes according to the invention by metal-catalysed addition (hydrosilylation) of 1-alkenes over trimethylsiloxy-terminated methylhydrogenpolysiloxane or cyclic methylhydrogensiloxanes via subsequent acid-catalysed equilibration with hexamethyldisiloxane (Bogdan Marciniec (Ed.) Comprehensive Handbook on Hydrosilylation, Pergamon Press, Oxford, 1992, p. 99 ff.). Suitable metals are Ni, Rh, Ru or Pt, preferably Pt, in the form of the colloidal metals themselves, their salts or complexes with the formal oxidation state 0 to VI.

The invention further relates to the use of at least one of the above-mentioned siloxanes in compositions which are chosen from the group which includes: cosmetic preparations, skincare products, sunscreen products, hair care products, deodorants, antiperspirants, products of decorative cosmetics, lipsticks, mouth care products and nail care products. In addition, the invention relates to the use of one of the abovementioned siloxanes in the dry cleaning of textiles. In addition, the invention relates to product compositions comprising one of the abovementioned siloxanes together with active ingredients and/or auxiliaries customary for the product. Examples of such product compositions are, for example, the formulations specified above. In the applications and product compositions specified above, the siloxanes used according to the invention may expediently be used in amounts of from 0.01 to 99% by weight, based on the total weight of the formulation and the product composition. Preference is given to a use in amounts of from 0.5 to 70% by weight, particularly preferably in amounts of from 1.0 to 60% by weight.

The abovementioned siloxanes used according to the invention are preferably used in cosmetic formulations of all types. Preferably, the siloxanes are used in amounts of from 0.01% to 99% in cosmetic preparations, such as, for example, deodorants, antiperspirants, decorative cosmetics, creams, lotions, skincare oils, shampoos, conditioners, sprays, aerosols, powders, sun care products, gels or pastes inter alia as vaporizable carrier.

In particular it is preferred to use no further cyclosiloxanes of any type in these formulations.

The siloxanes used according to the invention exhibit excellent compatibility with current cosmetic raw materials. They mix both with vegetable oils, such as sunflower oil, avocado oil, or jojoba oil, and with esters, such as isopropyl myristate, ethylhexyl palmitate or isononyl isononanoate. Moreover, the siloxanes according to the invention are soluble in alcohols, such as ethanol and isopropanol, and the non-cyclic siloxanes listed in accordance with INCI, such as Dimethicone, Phenyl Trimethicone or Bis-Phenylpropyl-Dimethicone.

BRIEF DESCRIPTION OF THE DRAWINGS

FIG. 1 depicts the vaporization behavior, measured in accordance with DIN 53249, of octamethylcyclotetrasiloxane, decamethylcyclopentasiloxane and the compounds of Examples 1 and 3 as non-vaporized residue in [%].

The examples below are intended to illustrate the use of the substances according to the invention without limiting their possible use as best possible D4 substitute.

EXAMPLES

Example 1

Preparation of 1,1,1,3,5,5,5-heptamethyl-3-ethyltrisiloxane 3900 g of water are initially introduced into a flask which is cooled with water and equipped with base drain outlet, stirrer, thermometer, reflux condenser and dropping funnel, and 1430 g (10 mol) of methylethyldichlorosilane are metered in with stirring. By regulating the metering rate, the temperature is limited to a maximum of 40° C. When the metered addition is complete, the stirrer is switched off and after a clear phase separation has developed, the lower, aqueous, hydrochloric acid phase is separated off and discarded. The upper oil phase is washed once with water and then transferred to a flask equipped with stirrer, thermometer, water separator and reflux condenser. 3240 g (20 mol) of hexamethyldisiloxane and 40 g (0.41 mol) of 98-100% strength sulphuric acid are added to the oil phase. The mixture is heated to the reflux temperature to condense the silanol groups and to remove residual water. After reflux for two hours, 10 g (0.047 mol) of perfluorobutanesulphonic acid are added and the reaction mixture is stirred for a further 4 h at 100° C. After cooling to below 70° C., to neutralize the mixture, 80 g of soda, 15 g of water and 3 g of 25% strength ammonia solution are added, the mixture is after-stirred for one hour and, after checking for freedom from acid, is heated again to the reflux temperature. After reflux for one hour, the mixture is cooled and filtered. This gives 3820 g of a crude product consisting of 58% hexamethyldisiloxane, 23% 1,1,1,3,5,5,5-heptamethyl-3-ethyltrisiloxane and oligomeric siloxanes which, as a result of fractional distillation, produces 717 g of 98%-pure 1,1,1,3,5,5,5-heptamethyl-3-ethyltrisiloxane with a boiling temperature of 169-172° C. Bottoms and separated-off hexamethylsiloxane can be passed to further equilibrations.

Example 2

Preparation of 1,1,1,3,5,5,5-heptamethyl-3-propyltrisiloxane 2000 g (=30 mol of SiH) of a distillate produced in the industrial preparation of linear trimethylsiloxy-terminated methylhydrogenpolysiloxanes, consisting of 75% cyclic methylhydrogensiloxanes with an average ring size of 4.8 $D^H$ units and 25% trimethylsiloxy-terminated methylhydrogensiloxanes with an average chain length of 3 (=MeSiHO) units are initially introduced into a heatable 4 l enamel autoclave equipped with stirrer and thermometer, and blanketed with nitrogen. The pressure in the autoclave is reduced to 100 mbar using a vacuum pump, the autoclave contents are heated to 65° C., 1 g of a commercial Pt$^0$ octanal/octanol complex containing 2% platinum (Gelest) is diluted with 20 ml of hexamethyldisiloxane and aspirated into the autoclave and the pressure in the autoclave is again reduced to 100 mbar. Propene is then introduced from a steel cylinder at a rate such that the pressure does not exceed 2 bar and the temperature, as a result of the virtually immediately recognizable exothermic reaction, does not exceed 130° C. After the exothermie has subsided, the mixture is after-stirred for a further 1 h at 130° C. and a propene pressure of 2 bar, the autoclave is decompressed and degassed. This gives 3300 g of adduct with an SiH content of <0.01 mmol/g.

658 g (6 mol of $D^{prop}$ (=propylMeSiO)$_n$) of the product obtained in this way and 1458 g (9 mol) of hexamethyldisiloxane are initially introduced into a flask equipped with stirrer, thermometer, water separator, reflux condenser and nitrogen blanketing, admixed with 102 g of Tonsil Standard 310 FF bleaching earth (Südchemie) and stirred for 6 h at a bottoms temperature of about 100° C. at the water separator, cooled and filtered. This gives 2100 g of a crude product consisting of 62% hexamethyldisiloxane, 14% 1,1,1,3,5,5,5-heptamethyl-3-propyltrisiloxane and 24% oligomeric siloxanes which, as result of fractional distillation, produces 410 g of 98%-pure 1,1,1,3,5,5,5-heptamethyl-3-propyltrisiloxane with a boiling temperature of 192-194° C. Bottoms and separated-off hexamethyldisiloxane can be passed to further equilibrations.

Example 3

Preparation of 1,1,1,3,3-pentamethyl-3-butyldisiloxane 2010 g (=30 mol of SiH) of 1,1,3,3-tetramethyldisiloxane are initially introduced, under nitrogen blanketing, into a heatable 4 l enamel autoclave equipped with stirrer and thermometer. The pressure in the autoclave is reduced to 250 mbar using a vacuum pump, the autoclave contents are heated to 65° C., 1 g of a commercial Pt$^0$octanal/octanol complex containing 2% platinum (Gelest) is diluted with 20 ml of hexamethyldisiloxane and aspirated into the autoclave. 1-Butene is then introduced from a steel cylinder at a rate such that the pressure does not exceed 2 bar and the temperature, as result of almost immediately recognizable exothermic reaction, does not exceed 130° C. After the exothermie has subsided, the 2-butene formed is stripped off up to 100 mbar, then 1-butene is again introduced and the mixture is after-stirred for a further 1 h at 130° C. and a butene pressure of 2 bar, the autoclave is decompressed, and degassed to 100 mbar. This gives 3500 g of adduct with an SiH content of <0.01 mmol/g.

984 g of adduct (8 mol of M$^{butyl}$ (=butyl-Me$_2$SiO$_{0.5}$) and 1312 (8 mol) of hexamethyldisiloxane are initially introduced into a flask equipped with stirrer, thermometer, water separator, reflux condenser and nitrogen blanketing, admixed with 0.1% sulphuric acids and 0.05% perfluorobutanesulphonic acid, neutralized for 4 h at a bottom temperature of 70° C. with 20 g of calcined soda, 3 g of water and 0.5 g of 25% strength NH$_3$ solution, distilled to 110° C., cooled and filtered. This gives 1950 g of a crude product consisting of 36% hexamethyldisiloxane, 47% 1,1,1,3,3-pentamethyl-3-butyldisiloxane and 17% 1,1,3,3-tetramethyl-1,3-dibutyldisiloxane, which, as result of fractional distillation, produces 810 g of 97%-pure 1,1,1,3,3-pentamethyl-3-butyldisiloxane with a boiling temperature of 166-169° C. Bottoms and separated-off hexamethyldisiloxane can be passed to further equilibrations.

Example 4

Vaporization Behaviour

Table 1 and FIG. 1 below give the vaporization behaviour, measured in accordance with DIN 53249, of octamethylcyclotetrasiloxane, decamethylcyclopentasiloxane and the example compounds 1 and 3 as non-vaporized residue in [%].

TABLE 1

Vaporization behaviour in accordance with DIN 53249 measured as remaining siloxane residue

| Time [min] | Octamethylcyclo-tetrasiloxane [%] | Decamethylcyclo-pentasiloxane [%] | Example 1 [%] | Example 3 [%] |
|---|---|---|---|---|
| 0 | 100 | 100 | 100 | 100 |
| 5 | 68.3 | | 59.7 | |
| 10 | 37.4 | | 23.9 | 82 |
| 15 | 11.4 | | 2.8 | |
| 20 | 0 | | 0.6 | 63 |
| 25 | 0 | | 0.1 | |
| 30 | 0 | 70.2 | 0.1 | 43 |
| 35 | 0 | | 0.1 | |
| 40 | | | | 25 |
| 50 | | | | 11 |
| 60 | | 39.6 | | 3 |
| 70 | | | | 0 |
| 90 | | 14.5 | | |
| 120 | | 1.2 | | |
| 150 | | 0 | | |

In contrast to octamethylcyclotetrasiloxane, decamethylcyclopentasiloxane vaporizes at a significantly slower rate, meaning that when formulations containing decamethylcyclopentasiloxane are applied, a greasy, wet feel arises on the skin. This is avoided when using Example compound 1, which exhibits a vaporization behavior analogous to that of octamethylcyclotetrasiloxane. Moreover, formulations which comprise Example compound 1 convey a very pleasant silky, non-greasy and light feel on the skin.

The volatility of Example compound 2 is between that of octamethylcyclotetrasiloxane and decamethylcyclopentasiloxane and can therefore be used when a volatility is required which should be between that of octamethylcyclotetrasiloxane and decamethylcyclopentasiloxane. Formulations which comprise Example compound 2 have a more substantial and somewhat more greasy feel on the skin.

By mixing the siloxanes according to the invention, it is possible to establish in a targeted manner a certain desired volatility graduated relative to octamethylcyclotetrasiloxane, or a certain desirable feel on the skin which differs from D4.

Example 5

Preparation of a Cosmetic Spray

The typical auxiliaries in such compositions are, for example, those substances which are described in A. Domsch: Die kosmetischen Präparate [Cosmetic Preparations] Vol. I and II 4th edition Verl. für chem. Industrie, H. Ziolkowsky KG, Augsburg, and in the International Cosmetic Ingredient Dictionary and Handbook 7th Ed. 1997 by J. A. Wenninger, G. N. McEwen Vol. 1-4 by The Cosmetic, Toiletry and Fragrance Association Washington D.C.

Phase 1: PEG-8 beeswax (6.0%), Example compound 1 (5.5%), jojoba oil (5.5%), cocoglycerides (5.0%), oleyl erucate (4.0%).

Phase 2: Water (78.6%), guar hydroxypropyltrimonium chloride (0.3%), xanthan gum (0.1%), sodium lactate (2.0%), phenonip (0.4%).

The two phases were separated from one another and heated to 65° C. Then, with vigorous stirring, hot phase 1 is added to hot phase 2 and stirred for 10 minutes at 60° C. Cooling takes place at a reduced stirring rate.

Example 6

Preparation of a Foundation Make-up

Phase 1: Water (q.s.), xanthan gum (0.3%), propylene glycol (5.0%), triethanolamine (1.4%).

Phase 2: Glyceryl stearate SE (3.9%), isononyl isononanoate (3.0%), silicone oil SF 1555® GE silicones (8.5%), Example compound 2 (3%), dimethicone SF 1236® GE Silicones (1.0%), stearic acid (3.9%).

Phase 2: Glyceryl stearate SE (3.9%), isononyl isononanoate (3.0%), bis-phenylpropyl dimethicone (SF 1555® GE Silicones) (8.5%), Example compound 2 (3%), dimethicone (5000 cStk) SF 1236® GE Silicones (gum) (1.0%), stearic acid (3.9%).

Phase 3: Pigment blend (3.3%).

Phase 4: Preservative (q.s.).

Preparation: Xanthan gum is dispersed in water with vigorous stirring. The remaining constituents of Phase 1 are added and heated to 75 to 77° C. The constituents for Phase 2 are likewise mixed with vigorous stirring and heated to 75 to 77° C. Phase 2 is then added to Phase 1 and homogenized for 5 minutes at at least 70° C. Phase 3 is then added, homogenized again and cooled to 50° C. Finally, the preservative is added and cooled to 25° C. with slow stirring.

Example 7

Preparation of a Cream Foundation

Phase 1: C30-45 alkyl dimethicone (SF 1642® GE Silicones) (11.0%), cetearyl methicone (SF 1632® GE Silicones) (4.0%), stearic acid (11.5%), Example compound 3 (4.0%), lanolin (3.0%), Phase 2: Water (q.s.), propylene glycol (3.4%), triethanolamine (2.9%), preservative (q.s.).

Phase 3: Polymethylsilsesquioxane (Tospearl 145A® GE Silicones) (10%), pigment blend (18%).

Preparation: Phase 1 and Phase 2 are heated separately to 70° C. Phase 2 is then added to Phase 1 with stirring until the mixture has cooled. This mixture is then added to Phase 3 with slow stirring.

We claim:

1. A cosmetic formulation comprising one or more vaporizable carriers selected from the group consisting 1,1,1,5,5,5-hexamethyl-3,3-diethyltrisiloxane, 1,1,1,3,5,5,5-heptamethyl-3-ethyltrisiloxane, 1,1,3,3,5,5-hexamethyl-1,5-diethyltrisiloxane, 1,1,1,3,5,5,5-heptamethyl-3-propyltrisiloxane, 1,1,1,5,5,5-hexamethyl-3,3-dipropyltrisiloxane and 1,1,1,3,5,5,5-heptamethyl-3-butyltrisiloxane, with the proviso that the propyl and butyl groups may be linear or branched substituents and further comprising one or more cosmetically effective ingredients, and said formulation being suitable for topical application to human skin, lips, nails and hair.

2. The cosmetic formulation of claim 1, wherein said one or more vaporizable carrier is 1,1,1,3,5,5,5-heptamethyl-3-ethyltrisiloxane.

3. The cosmetic formulation of claim 1, wherein said one or more vaporizable carrier is 1,1,1,3,5,5,5-heptamethyl-3-propyltrisiloxane.

4. The cosmetic formulation of claim 1, wherein said one or more vaporizable carrier is 1,1,1,3,5,5,5-heptamethyl-3-butyltrisiloxane.

5. The cosmetic formulation of claim 1 further comprising active ingredients and auxiliaries.

6. The cosmetic formulation of claim 1, wherein said vaporizable carriers are present in an amount of 0.01-99 wt. %.

7. The cosmetic formulation of claim 1, further comprising one or more members of the group consisting of dimethicones, phenyl trimethicone and bis-phenylpropyl dimethicone.

8. A sunscreen product, hair care product, deodorant, antiperspirant, product of decorative cosmetics, lipstick, mouth care product or nail care product comprising one or more vaporizable carriers selected from the group consisting 1,1,1,5,5,5-hexamethyl-3,3-diethyltrisiloxane, 1,1,1,3,5,5,5-heptamethyl-3-ethyltrisiloxane, 1,1,3,3,5,5-hexamethyl-1,5-diethyltrisiloxane, 1,1,1,3,5,5,5-heptamethyl-3-propyltrisiloxane, 1,1,1,5,5,5-hexamethyl-3,3-dipropyltrisiloxane and 1,1,1,3,5,5,5-heptamethyl-3-butyltrisiloxane, with the proviso that the propyl and butyl groups may be linear or branched substituents and further comprising one or more cosmetically or pharmaceutically effective ingredients, said formulation being suitable for application to human skin, lips, hair, mouth or nails.

9. The products of claim 8, wherein said vaporizable carriers are present in an amount of 0.01-99 wt. %.

10. A process for the preparation of 1,1,1,5,5,5-hexamethyl-3,3-diethyltrisiloxane, 1,1,1,3,5,5,5-heptamethyl-3-ethyltrisiloxane, 1,1,3,3,5,5-hexamethyl-1,5-diethyltrisiloxane, 1,1,1,3,5,5,5-heptamethyl-3-propyltrisiloxane, 1,1,1,5, 5,5-hexamethyl-3,3-dipropyltrisiloxane or 1,1,1,3,5,5,5-heptamethyl-3-butyltrisiloxane, which comprises conducting a metal-catalysed addition of a $C_2$-$C_4$-(1-alkene) over trimethylsiloxy-terminated methylhydrogenpolysiloxane or cyclic methylhydrogensiloxane, subjecting the product to an acid-catalysed equilibration with hexamethyldisiloxane, and enriching the product by distillation.

11. A method of cosmetic treatment which comprises applying a cosmetic composition comprising one or more vaporizable carriers selected from the group consisting 1,1,1,5,5,5-hexamethyl-3,3-diethyltrisiloxane, 1,1,1,3,5,5,5-heptamethyl-3-ethyltrisiloxane, 1,1,3,3,5,5-hexamethyl-1,5-diethyltrisiloxane, 1,1,1,3,5,5,5-heptamethyl-3-propyltrisiloxane, 1,1,1,5,5,5-hexamethyl-3,3-dipropyltrisiloxane and 1,1,1,3,5,5,5-heptamethyl-3-butyltrisiloxane to human skin, lips, nails, or hair, with the proviso that the propyl and butyl groups may be linear or branched substituents.

\* \* \* \* \*